United States Patent [19]

Frickel et al.

[11] 4,353,917
[45] * Oct. 12, 1982

[54] AMINO DERIVATIVES OF 2-METHYL-5-(2-HYDROXYSTYRYL)-1,3,4-THIADIAZOLE, THEIR PREPARATION, AND FORMULATIONS CONTAINING THESE COMPOUNDS

[75] Inventors: Fritz-Frieder Frickel, Deidesheim; Peter C. Thieme; Albrecht Franke, both of Wachenheim; Helmut Hagen, Frankenthal; Dieter Lenke, Ludwigshafen; Josef Gries, Wachenheim, all of Fed. Rep. of Germany

[73] Assignee: BASF Aktiengesellschaft, Fed. Rep. of Germany

[*] Notice: The portion of the term of this patent subsequent to Dec. 2, 1997, has been disclaimed.

[21] Appl. No.: 199,834

[22] Filed: Oct. 23, 1980

[30] Foreign Application Priority Data

Oct. 26, 1979 [DE] Fed. Rep. of Germany ....... 2943406

[51] Int. Cl.³ .................. A61K 31/41; A61K 31/425; C07D 285/12

[52] U.S. Cl. .................................. 424/270; 424/232; 542/428; 542/429; 542/458

[58] Field of Search ...................... 542/429, 458, 428; 424/270, 232

[56] References Cited

U.S. PATENT DOCUMENTS

| | | | |
|---|---|---|---|
| 3,432,545 | 3/1969 | Howe | 564/349 |
| 3,641,152 | 2/1972 | Shavel et al. | 564/349 |
| 4,006,184 | 2/1977 | Ilvespaa | 564/349 |
| 4,237,278 | 12/1980 | Thieme et al. | 542/458 |

FOREIGN PATENT DOCUMENTS

| | | |
|---|---|---|
| 1939809 | 2/1971 | Fed. Rep. of Germany. |
| 2624918 | 12/1977 | Fed. Rep. of Germany. |
| 1307436 | 2/1973 | United Kingdom. |

*Primary Examiner*—Alton D. Rollins
*Attorney, Agent, or Firm*—Keil & Witherspoon

[57] ABSTRACT

Novel aminopropanol derivatives of 2-methyl-5-(2-hydroxystyryl)-1,3,4-thiadiazole and their addition salts with acids, their preparation, pharmaceutical formulations containing these compounds, and their use as drugs in the treatment of coronary heart disease, hypertonia and cardiac arrhythmias.

4 Claims, No Drawings

AMINO DERIVATIVES OF 2-METHYL-5-(2-HYDROXYSTYRYL)-1,3,4-THIADIAZOLE, THEIR PREPARATION, AND FORMULATIONS CONTAINING THESE COMPOUNDS

The present invention relates to novel aminopropanol derivatives of 2-methyl-5-(2-hydroxystyryl)-1,3,4-thiadiazole, their addition salts with acids, their preparation, pharmaceutical formulations containing these compounds and their use as drugs in the treatment of coronary heart disease, hypertonia and cardiac arrhythmias.

We have found that compounds of the general formula (I)

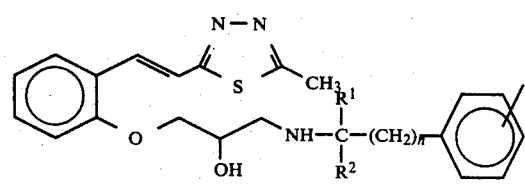

where n is 1 or 2, o is 1, 2 or 3, $R^1$ and $R^2$ are hydrogen or straight-chain or branched alkyl of 1 to 5 carbon atoms, $R^3$ is hydrogen, halogen, hydroxyl, alkyl, alkoxy or alkylthio of 1 to 5 carbon atoms (the last-mentioned three groups each being unsubstituted, or mono-, di- or tri-substituted by halogen, or mono-substituted by hydroxyl or alkoxy of 1 to 3 carbon atoms), alkenyl, alkynyl, alkynyloxy or cycloalkoxy, each of 2 to 6 carbon atoms in the alkyl and of 3 to 8 carbon atoms in the ring, aralkoxy of 7 to 9 carbon atoms or amino which is unsubstituted or is mono- or di-substituted by alkyl of 1 to 5 carbon atoms, and if o is 2 or 3, the $R^3$'s may be identical or different, or $R^3$ is methylenedioxy or alkylene of 3 or 4 carbon atoms, and their addition salts with acids, possess valuable pharmacological properties.

For $R^3$, examples of halogen are fluorine and chlorine, examples of unsubstituted and substituted alkyl, alkoxy and alkylthio are methyl, ethyl, propyl, n-butyl, tert.-butyl, methoxy, ethoxy, propoxy, trifluoromethyl, hydroxymethyl, 1-hydroxyethyl, methoxymethyl, ethoxymethyl, 1-methoxyethyl and n-propoxymethyl, examples of unsaturated radicals are vinyl, allyl and propargyloxy, examples of cycloalkoxy are cyclopentoxy and cyclohexoxy, and an example of aralkoxy is benzyloxy.

If $R^3$ is trimethylene or tetramethylene, the compound is an indanyl or tetrahydronaphthyl derivative.

Amongst the meanings mentioned, the preferred meanings of $R^1$ and $R^2$ are hydrogen and methyl and the preferred meanings of $R^3$ are hydrogen, chlorine, trifluoromethyl, alkyl of 1 to 4 carbon atoms, methoxy, hydroxyl or benzyloxy, the $R^3$'s, if two or three are present, being identical or different.

Accordingly, examples of compounds according to the invention are: 2-methyl-5-[2-[2-hydroxy-3-(2-(3,4-dimethoxyphenyl)-1-methylethylamino)-propoxy]-styryl]-1,3,4-thiadiazole, 2-methyl-5-[2-[2-hydroxy-3-(3-phenyl-1-methylpropylamino)-propoxy]-styryl]-1,3,4-thiadiazole, 2-methyl-5-[2-[2-hydroxy-3-(3-(4-hydroxyphenyl)-1-methylethylamino)-propoxy]-styryl]-1,3,4-thiadiazole, 2-methyl-5-[2-[2-hydroxy-3-(3-(4-benzyloxyphenyl)-1-methylethylamino)-propoxy]-styryl]-1,3,4-thiadiazole, 2-methyl-5-[2-[2-hydroxy-3-(3-(4-hydroxyphenyl)-1,1-dimethylpropylamino)-propoxy]-styryl]-1,3,4-thiadiazole, 2-methyl-5-[2-[2-3-(3-(4-methoxyphenyl)-1,1-dimethylpropylamino)-propoxy]-styryl]-1,3,4-thiadiazole, 2-methyl-5-[2-[2-hydroxy-3-(2-(4-chlorophenyl)-1,1-dimethylethylamino)-propoxy]-styryl]-1,3,4-thiadiazole, 2-methyl-5-[2-[2-hydroxy-3-(2-(3-trifluoromethylphenyl)-1,3-dimethylethylamino)-propoxy]-styryl]-1,3,4-thiadiazole, 2-methyl-5-[2-[2-hydroxy-3-(2-(4-hydroxyphenyl)-ethylamino)-propoxy]-styryl]-1,3,4-thiadiazole, 2-methyl-5-[2-[2-hydroxy-3-(2-(4-methoxyphenyl)-1,1-dimethylethylamino)-propoxy]-styryl]-1,3,4-thiadiazole, 2-methyl-5-[2-[2-3-(2-(2-methoxyphenyl)-1,1-dimethylethylamino)-propoxy]-styryl]-1,3,4-thiadiazole, 2-methyl-5-[2-[2-hydroxy-3-(2-(4-hydroxyphenyl)-1,1-dimethylethylamino)-propoxy]-styryl]-1,3,4-thiadiazole, 2-methyl-5-[2-[2-hydroxy-3-(3-(4-hydroxy-3-methoxyphenyl)-1-methylpropylamino)-propoxy]-styryl]-1,3,4-thiadiazole and 2-methyl-5-[2-[2-hydroxy-3-(3-(4-hydroxy-2-methyl-5-tert.-butylphenyl)-1-methylpropylamino)-propoxy]-styryl]-1,3,4-thiadiazole.

To prepare a compound according to the invention, a 2-methyl-5-(2-hydroxy-styryl)-1,3,4-thiadiazole of the general formula (II)

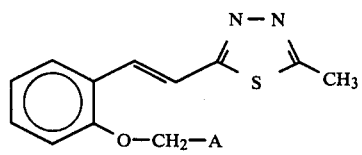

where A is

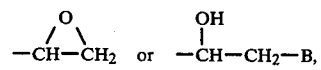

B being a nucleofugic leaving group, is reacted with an amine of the general formula (III)

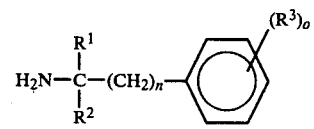

where $R^1$, $R^2$, RHU 3, n and o have the meanings given for formula I, in a conventional manner, advantageously in a solvent and in the presence or absence of an acid acceptor, the compound obtained being converted, if required, into an addition salt with a physiologically tolerated acid.

The leaving group B is preferably halogen, especially chlorine, bromine or iodine. Further examples of suitable nucleofugic leaving groups are aromatic and aliphatic sulfonic acid radicals, eg. the p-toluenesulfonic acid, p-bromobenzenesulfonic acid or methanesulfonic acid radical.

The reaction is carried out from 10° to 120° C., ie. at room temperature or above, advantageously at from 50° to 120° C., under atmospheric pressure or in a closed vessel under superatmospheric pressure, with or without heating at a temperature within the stated range.

The starting compounds may be reacted direct, ie. without addition of a diluent or solvent. Advantageously, however, the reaction is carried out in the presence of an inert diluent or solvent, for example a lower alcohol of 1 to 4 carbon atoms, eg. methanol, ethanol or a propanol, isopropanol and ethanol being preferred, a lower saturated dialkyl ether or cyclic ether, eg. diethyl ether, 1,2-dimethoxyethane, tetrahydrofuran or dioxane, benzene or an alkylbenzene, eg. toluene or xylene, an aliphatic hydrocarbon, eg. hexane, heptane or octane, a lower aliphatic ketone, eg. acetone, methyl ethyl ketone or methyl isobutyl ketone, a dialkylformamide, eg. dimethylformamide or diethylformamide, dimethyl sulfoxide or water, or a mixture of the said solvents.

Preferred solvents for the reaction of 2-methyl-5-[2-(2,3-epoxypropoxy)-styryl]-1,3,4-thiadiazole with one of the above amines (III) are lower alcohols, especially ethanol and isopropanol, the reaction preferably being carried out at from 50° C. to 120° C. under atmospheric pressure. In the case of the nucleophilic replacement of a radical B, preferred solvents are lower aliphatic ketones, eg. acetone and methyl isobutyl ketone, cyclic ethers, especially tetrahydrofuran and dioxane, and dialkylformamides, eg. dimethylformamide, and the reaction is preferably carried out at from 90° to 120° C. A catalytic amount of sodium iodide or potassium iodide may or may not be employed in the reaction.

A mixture of an epoxide and a halohydrin may also be employed as the starting compound of the formula II, since such mixtures are under certain circumstances formed in the industrial manufacture of a compound of the formula II.

In an advantageous embodiment of the nucleophilic replacement of the radical B by the amine used, the reaction is carried out in the presence of a base as an acid acceptor. Preferred bases are alkali metal hydroxides, carbonates, bicarbonates and alcoholates, and tertiary organic amines, such as pyridine or a trialkylamine, eg. trimethylamine or triethylamine. Amongst the alkali metal compounds, those of sodium or potassium are particularly suitable. The base is employed in stoichiometric amount or in slight excess. It can be advantageous to use an excess of the amine III employed for the reaction, so that it also serves as the acid acceptor.

The time required to complete the reaction depends on the reaction temperature and is in general from 2 to 15 hours. The product can be isolated in a conventional manner, for example by filtration or by distillation of the diluent or solvent from the reaction mixture. Purification of the compound obtained is effected in a conventional manner, for example by recrystallization from a solvent, conversion to a salt with an acid, or column chromatography.

The starting compounds of the formula (II) may be obtained by alkylating 2-methyl-5-(2-hydroxystyryl)-1,3,4-thiadiazole (which can be prepared by condensing salicylaldehyde with 2,5-dimethyl-1,3,4-thiadiazole) with an epihalohydrin or an α,ω-dihalo-porpan-2-ol. Suitable epihalohydrins are epichlorohydrin, epibromohydrin and epiiodohydrin and suitable α,ω-dihalo-propan-2-ols are, in particular, 1,3-dichloro-propan-2-ol and 1,3-dibromo-propan-2-ol.

Because of their carbon-carbon double bond, the novel compounds of the formula I can be in the form of mixtures of the cis- and trans-isomers, which can be separated by conventional physico-chemical methods, for example by fractional crystallization, chromatography or sublimitation.

The novel compounds of the formula (I) possess a chirality center on carbon atom 2 of the aliphatic aminopropanol side chain and are obtained as racemates which can be separated into the optically active antipodes by conventional methods, for example by formation of diastereomeric salts with optically active auxiliary acids, such as dibenzoyltartaric acid, camphor-10sulfonic acid, ditoluyltartaric acid or 3-bromocamphor-8-sulfonic acid and separation of these salts by crystallization.

Depending on the choice of the particular amine (III), some of the novel compounds of the formula (I) may have a second asymmetric carbon atom and can then be in the form of diastereomer mixtures which can be separated into diastereomer pairs by physico-chemical methods, in a conventional manner. Optically pure forms of the novel compounds (I) possessing two chirality centers can be obtained if an optically active amine of the general formula (III) is employed and the two diastereomers are subsequently separated, for example by fractional crystallization or chromatography.

If required, a novel compound obtained is converted to an addition salt with a physiologically tolerated acid. Examples of conventional suitable physiologically tolerated acids are, amongst inorganic acids, hydrochloric acid, hydrobromic acid, phosphoric acid and sulfonic acid, and, amongst organic acids, maleic acid, fumaric acid, lactic acid, tartaric acid, malic acid, citric acid, salicylic acid, adipic acid and benzoic acid; others may be found in Fortschritte der Arzneimittelforschung, published by Birkhäuser, Basel and Stuttgart, 10 (1966), 224–225, and J. Pharmac. Sci., 66 (1977), 1–5.

The addition of salts with acids are as a rule obtained in a conventional manner by mixing the free base or a solution thereof with the appropriate acid or a solution thereof in an organic solvent, for example lower alcohol, eg. methanol, ethanol or propanol, or a lower ketone, eg. acetone, methyl ethyl ketone or methyl isobutyl ketone, or an ether, eg. diethyl ether, tetrahydrofuran or dioxane. To cause better crystallization, mixtures of the above solvents may also be used. Furthermore, pharmaceutically useful aqueous solutions of addition salts of the aminopropanol derivatives of the general formula (I) with acids may be prepared by dissolving a free base of the general formula (I) in an aqueous acid solution.

The novel compounds, and their physiologically tolerated addition salts with acids, exhibit valuable pharmacological properties and are suitable for use as drugs, having a β-sympatholytic action, for the treatment of coronary heart disease (angina pectoris), hypertonia and cardiac arrhythmias.

The β-sympatholytic action was tested on cats. The comparative substance used was the known β-sympatholytic agent propranolol. The following methods were employed in the tests:

1. β-Sympatholytic action

Isoproterenol (1 μg/kg, administered intravenously) causes increases, averaging 40%, in the pulse rate of narcotized cats (weighing 2–4 kg). β-Sympatholytic agents inhibit such tachycardia. Isoproterenol was administered before, and 10 and 40 minutes after, the intravenous administration of the test substances. Linear relationships exist between the logarithms of the administered doses (mg/kg) of the test substances and the inhibition of isoproterenol-induced tachycardia (%). From these relationships, the doses (ED 50%) which inhibit the isoproterenol-induced tachycardia by 50% are determined.

2. Acute toxicity

To determine the dose which proves lethal in 50% of the animals (LD 50), the substances are administered intraperitoneally to female NMRI mice (weighing 19-26 g).

The novel compounds are distinguished by a high β-sympatholytic activity (cf. the Table). The cardiac $β_1$-receptors which are important in pharmacotherapy are blocked by doses which are as much as 5.6 (Example 2) or 6.7 (Example 4) times lower than those of the comparative substance propranolol. It follows from this high activity (ED 50%) and from the lethal dose (LD 50), which is of the same order of magnitude as that of propranolol, that the therapeutic range is 2.6 (Example 4) and 4.2 (Example 2) times greater than for propranolol.

TABLE $β_1$-Sympatholytic action and acute toxicity

| Compound | $β_1$-Sympatholytic action[1] | | Acute toxicity | Therapeutic |
| --- | --- | --- | --- | --- |
|  | ED 50%[2] | R.A.[3] | LD 50[4] | range[5] |
| Example 2 | 0.025 | 5.64 | 81.3 | 3,252 |
| Example 4 | 0.021 | 6.71 | 41.7 | 1,986 |
| Propranolol | 0.141 | 1.00 | 108 | 766 |

[1] Inhibition of isoproterenol-induced tachycardia. Cats under hexobarbital narcosis. Intravenous administration.
[2] Dose (mg/kg), which inhibits the isoproterenol-induced tachycardia by 50%.
[3] Relative activity. Propranolol = 1.00
[4] Mice. Intraperitoneal administration
[5] $\frac{LD\ 50}{ED\ 50\%}$
[6] Propranolol = 1.00

Accordingly, the present invention also relates to therapeutic agents or formulations which contain a compound of the formula (I) or a physiologically tolerated acid addition salt thereof, as the active compound, together with conventional carriers and diluents, and to the use of the novel compounds for therapeutic purposes.

The therapeutic agents or formulations are prepared in a conventional manner by compounding an apropriate dose with the conventional liquid or solid carriers or diluents and the conventional pharmaceutical auxiliaries, in accordance with the desired route of administration.

The preferred formulations are those suitable for oral administration. Examples of these are tablets, film tablets, dragees, capsules, pills, powders, solutions, suspensions or forms which have a depot effect.

Parenteral formulations, such as injection solutions, may of course also be used. Further examples of suitable formulations include suppositories.

Appropriate tablets may be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets may also consist of a plurality of layers.

Accordingly, dragees may be prepared by coating cores, prepared in a similar manner to the tablets, with agents conventionally used in dragee coatings, for example polyvinylpyrrolidone or shellac, gum arabic, talc, titanium dioxide or sugar. The dragee shell can also consist of several layers, in which the auxiliaries, mentioned above in connection with tablets, may be used.

Solutions or suspensions containing the novel active compounds may additionally contain sweeteners, eg. saccharin, cyclamate or sugar, and, for example, flavorings, such as vanillin or orange extract. They may furthermore contain suspending agents, such as sodium carboxymethylcellulose, or preservatives, such as p-hydroxybenzoates. Capsules containing the active compounds may be prepared, for example, by mixing the latter with an inert carrier, such as lactose or sorbitol, and encapsulating the mixture in gelatin capsules.

Suitable suppositories may be prepared, for example, by mixing the active compound with an appropriate carrier for this purpose, such as a neutral fat or polyethylene glycol or derivative thereof.

Individual doses of the novel compounds suitable for man are from 1 to 100 mg, preferably from 3 to 50 mg.

The Examples which follow illustrate the present invention.

I. Preparation of Starting Compounds

Compound 1

2-Methyl-5-(2-hydroxy-styryl)-1,3,4-thiadiazole 570 g (5 moles) of 2,5-dimethyl-1,3,4-thiadiazole and 275 g (2.5 moles) of salicylaldehyde are mixed and slowly heated to 150° C., whilst passing nitrogen through the mixture. After having been kept at 150° C. for 30 hours, the mixture is cooled, excess 2,5-dimethyl-1,3,4-thiadiazole is distilled off and the residue is recrystallized from methylglycol. 304 g of yellow crystals (56% of theory), of melting point 253°-254° C. are obtained.

$C_{11}H_{10}N_2OS$ (218): calculated: C, 60.6; H, 4.5; N, 12.8. found: C, 59.8; H, 4.6; N, 12.4.

Compound 2

2-Methyl-5-[2-(2,3-epoxypropoxy)-styryl]-1,3,4-thiadiazole 3.72 g (0.085 mole) of 55% strength sodium hydride in paraffin oil are suspended in 150 ml of absolute tetrahydrofuran and 18.6 g (0.085 mole) of 2-(2-hydroxystyryl)-5-methyl-1,3,4-thiadiazole in 200 ml of absolute hexamethylphosphorotriamide are then added dropwise in the course of 1.5 hours, at 0°-3° C. Thereafter the mixture is stirred for 1 hour at room temperature and 11.7 g (0.085 mole) of dibromohydrin are then added dropwise. The solution is left to stand for 16 hours at room temperature and is then poured into 1.5 liters of ice water and 0.5 liter of saturated sodium chloride solution. The solid obtained is filtered off and recrystallized from acetone. 11.8 g (51% of theory) of yellow crystals are obtained. Melting point 134°-135° C.

$C_{14}H_{14}N_2O_2S$ (274): calculated: C, 61.3; H, 5.1; O, 11.7; S, 11.7; N, 10.2. found: C, 61.3; H, 5.4; O, 13.5; S, 10.5; N, 8.4.

Compound 3

2-Methyl-5-[2-(2-hydroxy-3-chloropropoxy)-styryl]-1,3,4-thiadiazole 1 g of 2-methyl-5-[2-(2,3-epoxypropoxy)-styryl]-1,3,4-thiadiazole in a mixture of 100 ml of ethanol and 5 ml of a 3 N solution of hydrogen chloride in ether is left to stand for 12 hours. The precipitate formed is filtered off, washed neutral with ether and chromatographed over silica gel, using chloroform. The product eluates are evaporated to dryness, giving spectroscopically pure 2-methyl-5-[2-(2-hydroxy-3-chloropropoxy)-styryl]-1,3,4-thiadiazole of melting point 168°–170° C.

1H NMR spectrum (CDCl$_3$, TMS as internal standard): 2.5–3.3 (m, 6H), 4.8 (s, 1H), 5.5–6.0 (m, 3H and OH), 6.1–6.3 (m, 2H) and 7.3 (s, 3H)

II. Preparation of Compounds According to the Invention (The isolated compounds described in the Examples which follow are in each case the styryl derivative with the trans-configuration).

EXAMPLE 1

6.0 g of 2-methyl-5-[2-(2,3-epoxypropoxy)-styryl]-1,3,4-thiadiazole and 4.2 g of 2-(3,4-dimethoxyphenyl)-1-methylethylamine in 50 ml of isopropanol are refluxed for 6 hours. The residue which remains after distilling off the solvent is chromatographed over a silica gel dry column (about 500 g of silica gel/50 cm column length), using chloroform.

The residue obtained on evaporating the product eluates gives 3.1 g (28.9% of theory) of 2-methyl-5-{2-[2-hydroxy-3-(3,4-dimethoxyphenyl)-1-methylethylamino)-propoxy]-styryl}-1,3,4-thiadiazole monohydrate, of melting point 126°–127° C.

C$_{25}$H$_{31}$N$_3$O$_4$S.H$_2$O (487.62): calculated: C, 62.6; H, 6.7; N, 8.8. found: C, 62.9; H, 6.6; N, 8.6.

The compounds listed in the Table which follows are obtained in a similar manner from 2-methyl-5-[2-(2,3-epoxypropoxy)-styryl]-1,3,4-thiadiazole and the corresponding amines. All the compounds are characterized by elementary analyses and 1H NMR spectra.

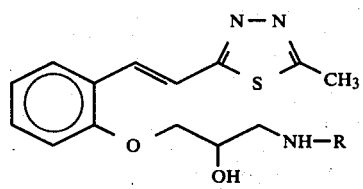

| No. | R | Salt form | Melting point (°C.) |
|---|---|---|---|
| 2 | —CH$_2$—CH$_2$—C$_6$H$_3$(OCH$_3$)(OCH$_3$) | free amine | 131–132 |
| 3 | —CH(CH$_3$)—CH$_2$—CH$_2$—C$_6$H$_5$ | free amine | 114–115 |
| 4 | —CH(CH$_3$)—CH$_2$—CH$_2$—C$_6$H$_4$—OH | HCl.H$_2$O | 169–171 |
| 5 | —CH(CH$_3$)—CH$_2$—CH$_2$—C$_6$H$_4$—OH | oxalic acid | 170–172 |
| 6 | —CH(CH$_3$)—CH$_2$—CH$_2$—C$_6$H$_2$(CH$_3$)(C(CH$_3$)$_3$)—OH | free amine | 156–160 |
| 7 | —CH(CH$_3$)—CH$_2$—CH$_2$—C$_6$H$_3$(OCH$_3$)—OH | free amine | 148–150 |
| 8 | —CH(CH$_3$)—CH$_2$—CH$_2$—C$_6$H$_4$—OCH$_2$—C$_6$H$_5$ | free amine | 112–115 |
| 9 | —C(CH$_3$)$_2$—CH$_2$—CH$_2$—C$_6$H$_4$—OH | 2HCl.H$_2$O | 140–142 |
| 10 | —C(CH$_3$)$_2$—CH$_2$—CH$_2$—C$_6$H$_4$—OCH$_3$ | 2HCl.2H$_2$O | 134–136 |
| 11 | —C(CH$_3$)$_2$—CH$_2$—C$_6$H$_4$—Cl | 2HCl.2H$_2$O | 166–168 |
| 12 | —C(CH$_3$)$_2$—CH$_2$—C$_6$H$_4$—CF$_3$ | free amine | 106–107 |
| 13 | —CH$_2$—CH$_2$—C$_6$H$_4$—OH | free amine ½H$_2$O | 177–178 |
| 14 | —C(CH$_3$)$_2$—CH$_2$—C$_6$H$_4$—OCH$_3$ | 2HCl | 188–189 |
| 15 | —C(CH$_3$)$_2$—CH$_2$—C$_6$H$_4$—OCH$_3$ | 2HCl | 198–199 |

III. Examples of Formulations

1. Tablets

| | | |
|---|---|---|
| (a) | An active compound of the formula 1 | 5 mg |
| | Lactose | 200 mg |
| | Methylcellulose | 15 mg |
| | Corn starch | 50 mg |
| | Talc | 11 mg |
| | Magnesium stearate | 4 mg |
| | | 285 mg |
| (b) | An active compound of the formula I | 20 mg |
| | Lactose | 178 mg |
| | Avicel | 80 mg |
| | Polywachs 6000 | 20 mg |
| | Magnesium stearate | 2 mg |
| | | 300 mg |
| (c) | An active compound of the formula I | 50 mg |

9

-continued

| | |
|---|---|
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 280 mg |

The active compound is moistened with a 10% strength aqueous solution of the polyvinylpyrrolidone, forced through a sieve of 1.0 mm mesh width and dried at 50° C. The granules obtained are mixed with polyethylene glycol (mean molecular weight 4,000), hydroxypropylmethylcellulose, talc and magnesium stearate and the mixture is molded to form tablets each weighing 280 mg.

2. Example of dragees

| | |
|---|---|
| An active compound of the formula I | 60 mg |
| Lactose | 90 mg |
| Corn starch | 60 mg |
| Polyvinylpyrrolidone | 6 mg |
| Magnesium stearate | 1 mg |
| | 217 mg |

The mixture of the active compound, lactose, corn starch and an 8% strength aqueous solution of the polyvinylpyrrolidone is granulated by forcing through a 1.5 mm sieve and the granules are dried at 50° C. and then forced through a 1.0 mm sieve. The granules from this operation are mixed with magnesium stearate and the mixture is molded to form dragee cores. The cores obtained are provided, in a conventional manner, with a coating which essentially consists of sugar and talc.

3. Capsule formulation

| | |
|---|---|
| An active compound of the formula I | 5 mg |
| Magnesium stearate | 2.0 mg |
| Lactose | 19.3 mg |

4. Injection solution

| | |
|---|---|
| An active compound of the formula I | 10 mg |
| Sodium chloride | 9 mg |
| Distilled water, q.s. to make up to 1.0 ml | |

We claim:

1. A compound of the general formula (I)

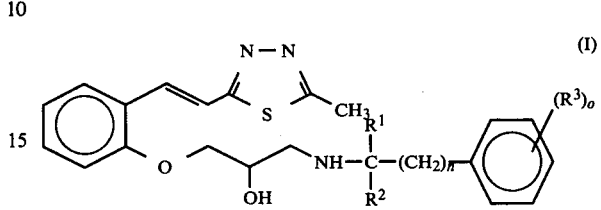

were n is 1 or 2, o is 1, 2 or 3, $R^1$ and $R^2$ are hydrogen or straight-chain or branched alkyl of 1 to 5 carbon atoms, $R^3$ is hydrogen, halogen, hydroxyl, alkyl, alkoxy or alkylthio of 1 to 5 carbon atoms (the last-mentioned three groups each being unsubstituted, or mono-, di- or tri-substituted by halogen, or mono-substituted by hydroxyl or alkoxy of 1 to 3 carbon atoms), alkenyl, alkynyl or alkynyloxy, each of 2 to 6 carbon atoms and cycloalkoxy of 3 to 8 carbon atoms, benzyloxy or amino which is unsubstituted or is mono- or di-substituted by alkyl of 1 to 5 carbon atoms, and if o is 2 or 3, the $R^3$'s may be identical or different, or $R^3$ is methylenedioxy or alkylene of 3 or 4 carbon atoms, and its addition salts with acids.

2. 2-Methyl-5-[2-[2-hydroxy-3-(2-(3,4-dimethoxyphenyl)-ethylamino)-propoxy]-styryl]-1,3,4-thiadiazole.

3. 2-Methyl-5-[2-[2-hydroxy-3-(3-(4-hydroxyphenyl)-1-methylpropylamino)-propoxy]-styryl]-1,3,4-thiadiazole.

4. A therapeutic agent for treating angina pectorus, hypertonia and cardiac arrhythmias which comprises: a pharmaceutically acceptable carrier or diluent and a therapeutically effective amount of a compound of the formula I of claim 1, or a physiologically tolerated acid addition salt thereof.

* * * * *